(12) United States Patent
Hilston et al.

(10) Patent No.: US 6,669,887 B2
(45) Date of Patent: *Dec. 30, 2003

(54) REVERSIBLY EXTENSIBLE FILM

(75) Inventors: Michael D. Hilston, Painesville, OH (US); Beverly S. Braun, Willoughby, OH (US); Robert A. Wanska, Thompson, OH (US)

(73) Assignee: Avery Dennison Corporation, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 404 days.

This patent is subject to a terminal disclaimer.

(21) Appl. No.: 09/742,642

(22) Filed: Dec. 21, 2000

(65) Prior Publication Data

US 2001/0001685 A1 May 24, 2001

Related U.S. Application Data

(62) Division of application No. 09/151,248, filed on Sep. 10, 1998, now Pat. No. 6,221,483.

(51) Int. Cl.[7] .............................................. B29C 47/06
(52) U.S. Cl. ............................. 264/173.15; 264/173.12
(58) Field of Search ....................... 264/173.15, 173.12, 264/148, 160

(56) References Cited

U.S. PATENT DOCUMENTS

| 3,485,912 | A | * | 12/1969 | Schrenk et al. | ........ 264/172.15 |
|---|---|---|---|---|---|
| 3,750,669 | A | | 8/1973 | DeLuca | ....................... 128/287 |
| 3,800,796 | A | | 4/1974 | Jacob | ......................... 128/284 |
| 4,020,842 | A | | 5/1977 | Richman et al. | ............ 128/287 |
| 4,051,853 | A | | 10/1977 | Egan, Jr. | ..................... 128/287 |
| 4,063,559 | A | | 12/1977 | Tritsch | ....................... 128/287 |
| 4,435,141 | A | | 3/1984 | Weisner et al. | .......... 425/131.1 |
| 4,460,364 | A | | 7/1984 | Chen et al. | .................. 604/387 |
| 4,463,046 | A | * | 7/1984 | Hutchison et al. | .......... 428/156 |
| 4,533,150 | A | * | 8/1985 | Hardy | ..................... 280/14.25 |
| 4,543,139 | A | | 9/1985 | Freedman et al. | .......... 156/152 |
| 4,554,191 | A | | 11/1985 | Korpman | ..................... 428/38 |
| 4,568,344 | A | | 2/1986 | Suzuki et al. | ............... 604/389 |
| 4,643,729 | A | | 2/1987 | Laplanche | ................... 604/389 |
| 4,769,199 | A | * | 9/1988 | Bemis et al. | ............... 264/139 |
| 4,787,897 | A | | 11/1988 | Torimae et al. | ............. 604/389 |
| 4,795,456 | A | | 1/1989 | Borgers et al. | ............. 604/390 |
| 5,057,097 | A | | 10/1991 | Gesp | .......................... 604/389 |
| 5,429,856 | A | | 7/1995 | Krueger et al. | ............. 604/370 |
| 5,589,542 | A | | 12/1996 | Himes | ......................... 525/98 |
| 5,779,691 | A | | 7/1998 | Schmitt | ....................... 604/386 |
| 6,098,247 | A | * | 8/2000 | Santelli, Jr. | .................. 16/225 |
| 6,221,483 | B1 | * | 4/2001 | Hilston et al. | ............... 428/343 |

FOREIGN PATENT DOCUMENTS

| CA | 1285730 | 7/1991 | |
|---|---|---|---|
| EP | 0 249 073 | 1/1992 | |
| EP | 0 247 855 | 3/1992 | |
| EP | 0 815 820 | 1/1998 | |
| JP | 59-155478 | 9/1984 | ............. C08L/9/00 |

* cited by examiner

Primary Examiner—Mark Eashoo
(74) Attorney, Agent, or Firm—Pearne & Gordon LLP

(57) ABSTRACT

A reversibly extensible polymeric film is hot formed, as by coextrusion, using selected polymeric materials that provide discrete areas of elastic and inelastic polymeric materials arranged in laterally spaced and longitudinally elongated lanes or stripes connected by integrally formed joints therebetween. The elastic materials comprise block polymers selected from tetrablock, triblock and diblock polymers, and the inelastic material is selected from polyolefins such as polyethylene, polypropylene, poly(ethylene-propylene), poly(ethylene-vinyl acetate), poly(styrene-butadiene), or copolymers or blends thereof.

22 Claims, 4 Drawing Sheets

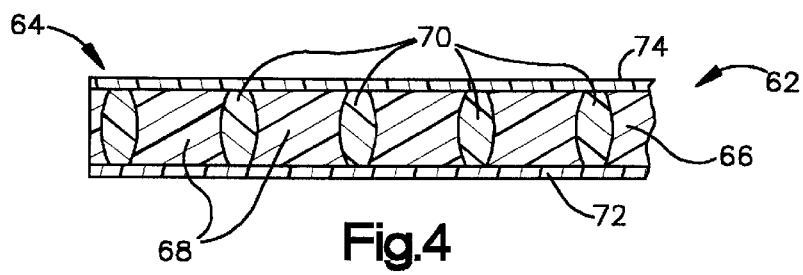
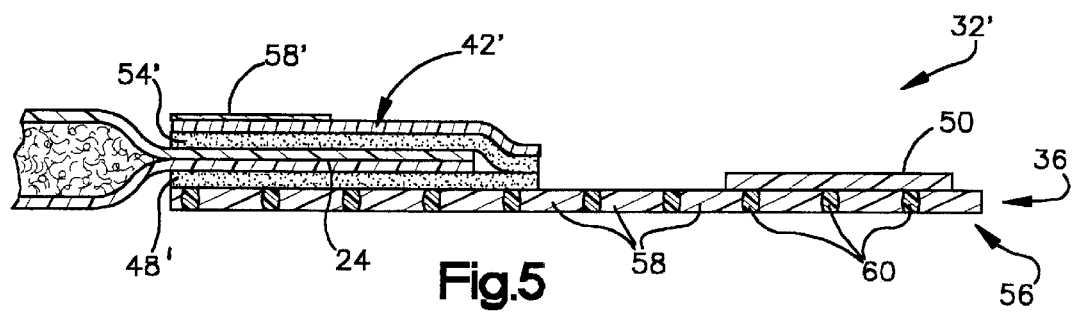
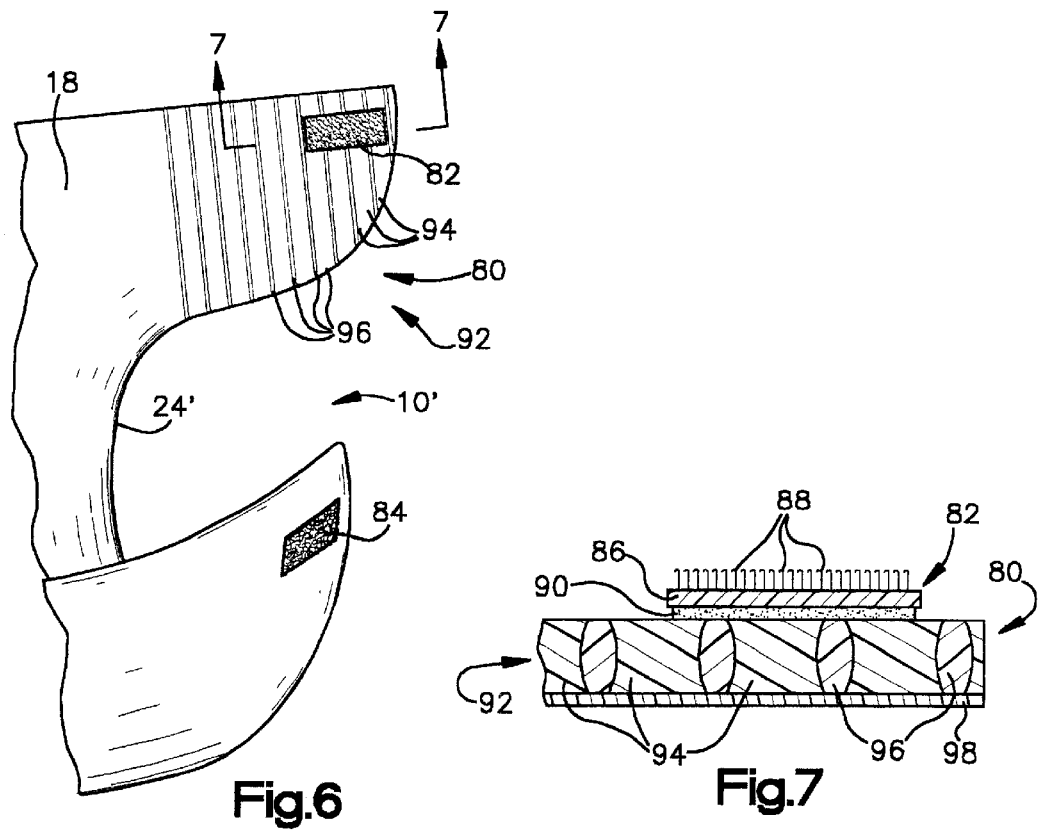

REVERSIBLY EXTENSIBLE FILM

This application is a division of application Ser. No. 09/151,245, filed Sep. 10, 1998, now U.S. Pat. No. 6,221, 483, dated Apr. 24, 2001.

BACKGROUND OF THE INVENTION AND RELATED ART

The present invention relates to flexible sheet or roll stock film having elastic characteristics and to products formed of such film. Film-forming polymers are used to hot form the film with elastic and nonelastic or inelastic discrete polymer portions connected at a joint therebetween.

The films are useful in tapes, closure devices, labels and other constructions requiring a stretchable or elastic film element. The shear resistance and elastic property of the film in combination with the non-creep nature of the inelastic portions provide unique and valuable performance useful in a wide range of applications. The films may be used as a construction film for forming an element of a more comprehensive tape or closure system including industrial or craft applications requiring pieces to be secured together with tension during a dry cycle or medical applications such as medical tapes, suture tapes, nasal dilators, bandages and the like.

The films are particularly useful as substrates for closure systems such as mechanical and/or self-adhesive diaper fastening tapes or tabs. In such applications, the elastic characteristic of the film enhances fit, comfort, absorbency, containment and/or security of closure. The films may also be used as attachments to the waist or leg areas of a device or article of clothing for enhancing fit, comfort, and/or sealing characteristics. The film is especially useful in connection with disposable diaper tape fastening systems, and it is specifically described with respect to the same hereinafter.

Disposable diapers are known in the art and comprise multiple layer assemblies or laminates including an inner filling of absorbent fiber or material sandwiched between outer layers. One of the outer layers includes an absorbent material to be disposed against the user, and the other outer layer may comprise a waterproof plastic film for containment of waste within the diaper.

The use of stretchable fastening tapes or tabs in disposable diapers is disclosed in U.S. Pat. No. 3,800,796 to Jacobs. In Jacobs, a polymeric variation of the tape includes a semielastic strip having a fully extensible elastic central segment and two non-extensible inelastic terminal segments. The elastic segment comprises a heat-sealable elastomer such as a butadiene-styrene block polymer. The patent does not describe a coextrusion process for making film that may be used to form the tape.

U.S. Pat. No. 4,787,897 to Torimae et al. discloses a co-extruded diaper fastening tape with an elastic central segment and nonelastic terminal segments. The elastic segment includes triblock polymers containing 10 to 80 parts of a processing aid comprising a hydrogenated terpene resin or alicyclic hydrocarbon having a melt or softening point of 80° C. and a molecular weight of 400 to 2000.

SUMMARY OF THE INVENTION

It has now been discovered that certain polymeric materials comprising thermoplastic elastomers may be used to form reversibly extensible sheets or roll film material. The sheets or films include discrete portions of thermoplastic elastomer having elastic characteristics joined with portions of thermoplastic polymer having nonelastic properties.

The thermoplastic elastomers and the thermoplastic polymers are film-forming polymers that may be hot formed as by simultaneous coextrusion. For example, the film-forming polymers may be co-extruded in a pattern of laterally spaced and longitudinally parallel polymer lanes or stripes extending in the machine direction with integrally formed joints adhering adjacent lanes together.

The film material according to the invention has excellent extrusion characteristics and superior joint strength between the elastic and the nonelastic polymers. Also, the film materials have improved elevated temperature shear properties and improved caliper and roll conformation as indicated by wound rolls of near cylindrical configuration.

The thermoplastic polymer may be a polyolefin such as polyethylene, polypropylene, poly(ethylene-propylene), poly(ethylene-vinyl acetate), poly(styrene-butadiene), or copolymers or blends thereof. A minor amount of an ethylene-propylene component may be incorporated in the thermoplastic polymer. Polypropylene is a preferred thermoplastic polymer. Films of such polymers, e.g. 0.1 to 20 mils thick, exhibit little or no recovery from stretching or deformation and exemplify the inelastic or nonelastic properties of interest herein.

Thermoplastic elastomers of interest herein are block copolymers having or containing the tetrablock structure A-B-A-D, the triblock structure A-B-A and, optionally, the diblock structure A-B in lesser amounts as a minor component. In such block structures, A represents a block which is non-rubbery or glassy or crystalline at service temperature, e.g. about 100° F. in the case of diaper tapes, and B and D, which may be the same, each represent a block which is rubbery or elastomeric at service temperature. At elevated temperatures, the A, B and D blocks are sufficiently fluid to enable coextrusion of the thermoplastic elastomer. Films of such polymers, e.g. 0.1 to 20 mils thick, exhibit recovery from stretching or deformation below their yield point and exemplify the elastic properties of interest herein.

The thermoplastic elastomer may be blended with a thermoplastic polymer end block reinforcing agent of relatively high molecular weight, e.g. a molecular weight greater than 2000 and, more preferably, in the range of 3000 to 5000, and higher. Such reinforcing agents improve elevated temperature shear strength. Most unexpectedly, such reinforcing agents have been found herein to increase the caliper or gauge uniformity of wide sheet coextrusions, e.g. 1500 mm or 60 inches.

Preferred reinforcing agents are high molecular weight aromatic compounds such as polyphenylene oxide (or polyphenyl ether) which have molecular weights in the range of 3,000 to 30,000 and higher. These reinforcing agents are added in amounts ranging from 3 to 9, and more preferably, from 8 to 9 parts by weight based on the weight of the elastomer component. Other preferred reinforcing agents comprise pure monomer resins of polycyclic arenes including substituted and unsubstituted vinylarenes such as styrene and methylstyrene. These are used in amounts ranging from 5 to 25, and more preferably, from 12 to 14 parts by weight based on the weight of the elastomer component.

Other conventional additives such as antioxidants, colorants and processing aids may be added to either or both the elastic and nonelastic polymers.

A diaper fastening tape should have the ability to withstand an applied load of 500 grams for more than 1,000 minutes at 100° F. (100° F. being used to simulate body temperature.) Some of the films in accordance with the invention have shear strengths that exceed 10,000 minutes at 100° F. under a 500 g load.

The reason for the improved shear strength is believed to be related to the unique nature of the joint at the joining plane or interface where the thermoplastic meets the tetrablock thermoplastic elastomer. The strength of the joint is believed to be improved by the unique interaction of the saturated tetrablock elastomer with the thermoplastic polymer. More particularly, preferred tetrablock elastomers include a terminal segment or free tail block of ethylene-propylene that provides a hydrocarbon structure similar to the hydrocarbon groups of the thermoplastic so as to favor interaction and improved joint strength. This effect may be further enhanced by addition to the thermoplastic of additional similar groups such as ethylene propylene rubber (EPR) which is used as an impact modifier. In contrast, elastic films made with conventional diblock and/or triblock thermoplastic elastomers do not develop such good joint strength.

Shear strength is improved also by the use of increased numbers of elastomer lanes of reduced size. For example, the shear strength of films having a 2" wide polyolefin lane and a ¼" wide rubber lane were greatly improved by reducing the lane widths to about ½" and 1/16" to ⅛". Generally, rubber lanes that are of such narrower dimension give much higher shear times. For example, a tape having a single rubber lane may give a time of 1,000–2000 minutes. A tape of the same material but with multiple more narrow lanes of rubber will yield upwards of 10,000 to 20,000 minutes. Generally, the elastomer lane width in a 3 to 8 mil thick film should be in the range of from about 1/16" to ⅛".

The foregoing improvement apparently relates to the division of work of elasticity into two or possibly more lanes. This is believed to be related to the facts that the propagation of a fracture due to the presence of a cut or nick is pulling rate dependent and that stresses within an elastomeric lane that is failing are focused on a very small portion of the elastomer. If there is only one elastomeric lane in the stretch zone of a tab that is being elongated, and that one lane has a nick or cut, the stresses associated with said elongation are very quickly focused on the point of crack propagation and complete failure occurs in a short time. If there is a multiplicity of elastomeric lanes, only one of which has a cut or nick, the propagation of a crack across the lane with the cut or nick is delayed because there are other, defect-free elastomeric lanes within the stretch portion of the tab that can accommodate the elongation without suffering failure. Ultimately, of course, as elongation or pulling rate increases to very high values, a tab will suffer failure, but at ordinary values the elastic response time of the defect-free lanes is short enough to substantially delay failure in the lane that has a defect.

The end block reinforcing agents herein are of relatively high molecular weight, i.e. greater than 2000, as compared with prior art, and they have been found also to contribute to the improved caliper and roll conformation. Heretofore, coextrusion of adjacent elastic and nonelastic polymer materials through a single die opening resulted in films having sufficiently different thicknesses in the different polymer areas to cause nonuniform and unacceptable roll conformation. This resulted in limited film widths that are commercially cost ineffective. For example, coextruded films in accordance with U.S. Pat. No. 4,787,897, supra, were found to have undesirable caliper variation in the width direction yielding unacceptable roll conformation. That is, the rolls are nonuniform and have varying diameter dimensions along the axis of the roll and, for example, may have gauge bands of increased thickness around its circumference at the locations of the elastomeric lanes. The gauge bands cause the elastomer to be distorted, which in turn, causes the film to bunch-up and develop wrinkles upon unwinding, processing and re-winding the roll. The poor roll conformation significantly limits the roll width, e.g., to that of one or two diaper tape widths, which is not acceptable for commercial manufacture.

The arrangement and sizes of the elastomer and nonelastomer polymer areas have been found also to provide improvements in roll conformation. Generally, improvements in roll conformation have been achieved by limiting the width of the elastomer portion. Also, improved roll conformation is achieved by providing increasing numbers of elastomer and nonelastomer portions of reduced size; i.e., an increased number of laterally more narrow lanes. Roll conformation is improved also with overall uniformity in the elastomer and nonelastomer arrangement across the entire width of the sheet.

The film optionally includes one or two thin skins of polymer that completely cover the adjacent lanes. That is, the distinct elastic and nonelastic polymer areas form substantially the entire thickness of the film, but a substantially thinner skin may be formed along one or both of the film surfaces. Thermoplastic skins are preferred since they will generally have less surface friction and will aid machine processing as compared with skins formed of thermoplastic elastomer. Also, thermoplastic skins will reduce, if not eliminate, the tendency of the film to block as by adherence of contacting elastomer lanes or polymer areas.

The thin film lowers the coefficient of friction on that side of the film on which it is present to provide handling advantages in web processing. The skin also provides a non-elastomeric surface on which to coat an adhesive, and this may be of particular advantage if the adhesive or other coating is not inherently stable over time when coated directly onto the surface of thermoplastic elastomers.

BRIEF DESCRIPTION OF THE DRAWINGS

FIG. 4 is a sectional view on enlarged scale taken along the line 4—4 in FIG. 1;

FIG. 5 is a sectional view similar to FIG. 2 showing a two piece diaper fastening tape in accordance with the invention;

FIG. 6 is a fragmentary perspective view showing another embodiment of a disposable diaper in accordance with the invention;

FIG. 7 is a sectional view on an enlarged scale taken along the line 7—7 in FIG. 6;

DETAILED DESCRIPTION OF THE DRAWINGS

Figure 1:
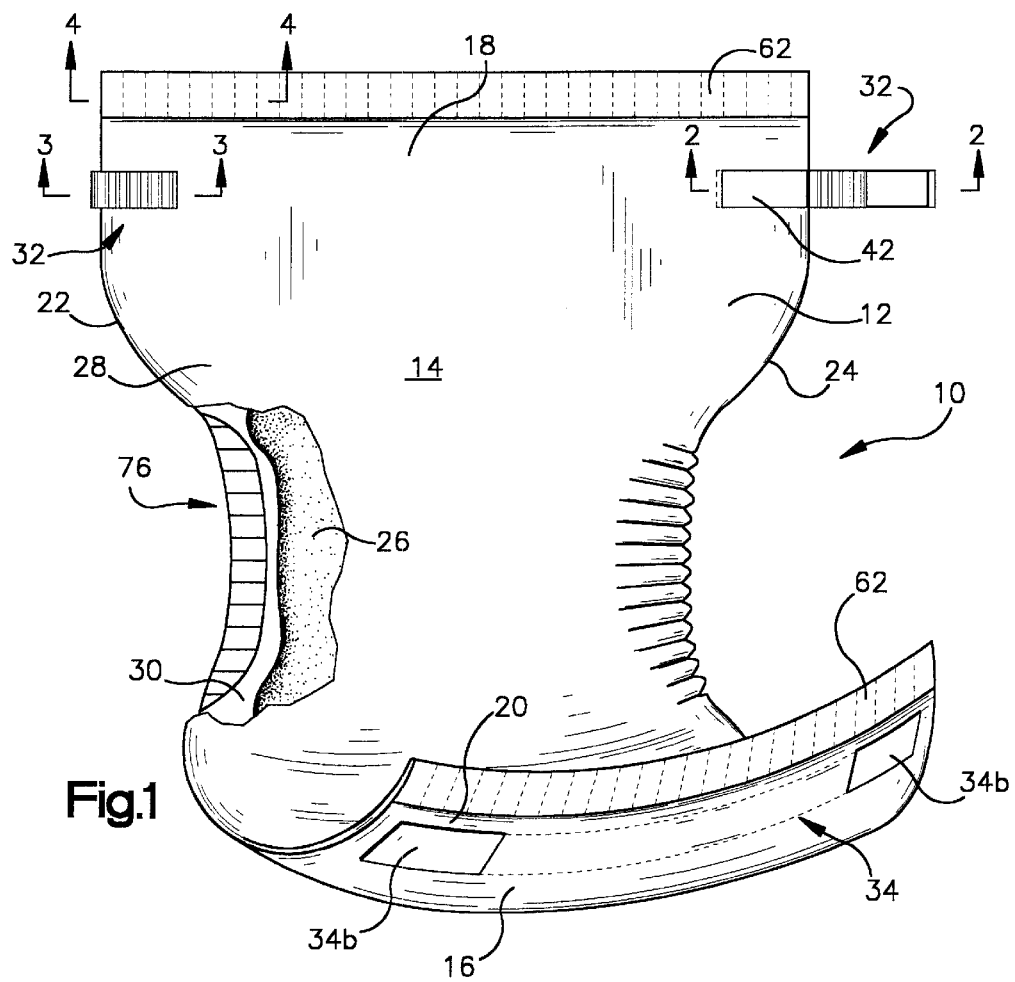
FIG. 1 is a perspective view of a disposable diaper having a tab fastener, waist band and leg cuff in accordance with the invention, with parts broken away.

Referring to FIG. 1, there is shown a disposable diaper 10 in accordance with the invention. The diaper 10 comprises a laminate or layered assembly 12 having an inside surface 14 and an outside surface 16. The diaper 10 has an hourglass configuration including a first end 18 and a second end 20 connected by longitudinally extending edges 22 and 24.

The layered assembly 12 includes a liquid absorbent pad or batt core 26 enclosed within a liquid permeable inner shell or top sheet 28 and a liquid impermeable outer shell or back sheet 30. The core 26 may be of slightly smaller dimensions than the shells 28 and 30 so as to cause the latter to form a perimeter or border about the core 26.

Figure 2:
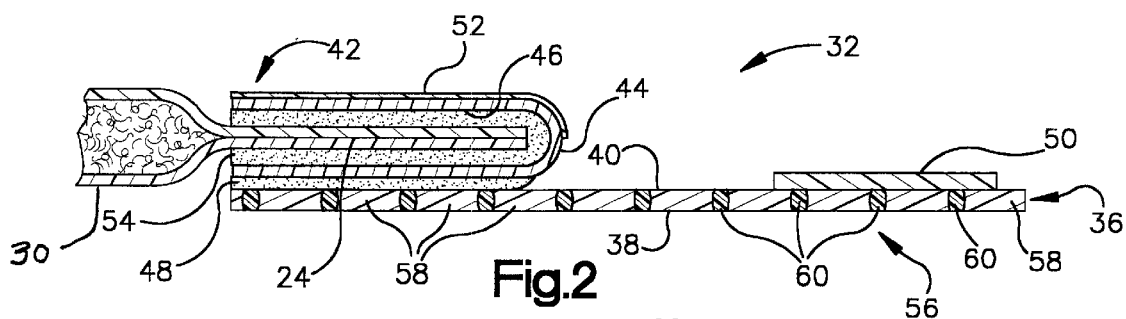
FIG. 2 is a sectional view on an enlarged scale taken along the line 2—2 in FIG. 1 showing that tab fastener in a deployed position.
Figure 3:
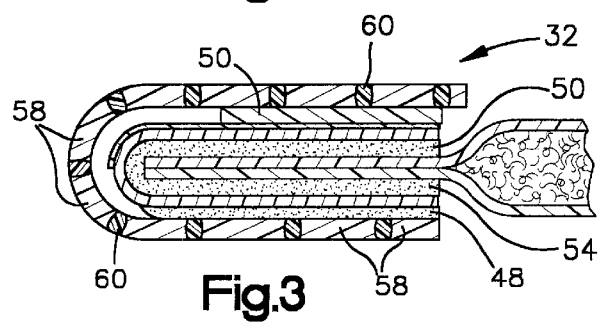
FIG. 3 is a sectional view on an enlarged scale taken along the line 3—3 in FIG. 1 showing the tab fastener in a storage position.

Referring to FIGS. 1, 2 and 3, the diaper 10 includes tab or tape fastener assemblies 32 secured to the first end 18 of the diaper adjacent associated longitudinal edges 22 and 24. The tabs 32 are arranged to provide side closure of the diaper 10 about an infant or user upon engagement with landing member or zone 34. The landing member 34 may comprise separate reinforcing tape members 34a and 34b as shown in solid outline or a single tape piece as shown by the combined solid and dotted outline in FIG. 1. As described in further detail below, the tabs 32 and landing member 34 may provide adhesive and/or mechanical closure of the diaper 10.

The tab 32 has a multilayer construction including a fastening element or tape 36 having an outer face 38 and an opposed inner face 40. The fastening tape 36 is secured to a release element or tape 42 having an outer face 44 and an inner face 46. The tapes 36 and 42 are assembled together in lengthwise alignment and adjacency in a conventional manner.

A proximal terminal end of the fastening tape 36 is secured by an adhesive layer 48 to the inner face 44 of the release tape 42. A pressure-sensitive adhesive layer 50 temporarily secures the distal end of the fastening tape 42 to the adjacent end of the release tape 42. In a known manner, a silicone or carbamate release coat 52 may be applied to the outer face 44 of the tape 42 to promote separation of the adhesive layer 50 and deployment of the fastening tape 36. The release tape 42 is secured by an adhesive layer 54 to the adjacent longitudinal edge 22 of the diaper 10.

The fastening tape 36 includes a substrate or backing film 56 which is reversibly extensible. The substrate 56 includes alternating inelastic lanes 58 and elastic lanes 60. As shown, the alternating lanes extend through the entire thickness of the substrate 56. Various widths of inelastic and elastic lanes may be selected, and the relative widths may vary along the length of substrate 56.

As is customary, the tab 32 is cut in a machine cross direction from a roll of stock material. Accordingly, the length of the tab 32 corresponds with the cross direction of the roll stock material and the width of the tab 32 corresponds with the machine direction of the roll stock. As explained more fully below, the alternating lanes 58 and 60 are located at laterally spaced locations along the entire length of the tab 32 and extend across the full width thereof.

The elastic lanes 60 which contact adhesive 48 or 50 do not contribute to the elasticity of the tab during use. Even though the elastic property of such lanes is not taken advantage of, it has been discovered that positioning alternating lanes of inelastic and elastic material across the entire width of the roll stock material enhances the roll conformation, enabling higher quality, and high speed manufacture of the same.

Referring to FIGS. 1 and 4, the diaper 10 includes a waist band 62 secured to each of the diaper ends 18 and 20. The waist band 62 provides elastic characteristics and insures a tight fit of the diaper about the user's waist. The waist bands 62 are secured to the longitudinal ends 18 and 20 of the diaper 10 in any convenient manner including, for example, sonic welding or adhesives. The waist band 62 may be disposed between the top sheet 28 and back sheet 30 of the diaper with appropriate gathering or pleating of the sheets 28 and 30 to allow for expansion and contraction of the diaper waist area.

Referring to FIG. 4, the waist band 62 is formed of a reversibly extensible multilayer film 64 having a core portion 66 formed of alternating elongate inelastic lanes or stripes 68 and elastic lanes or stripes 70. The film 64 includes opposed skins 72 and 74 extending along opposite surfaces thereof. (The thicknesses of the skins 72 and 74 are greatly exaggerated in FIG. 4.) The skins 72 and 74 may be formed of the same polymer as the inelastic lanes 68. The skins 72 and 74 provide the waist band 62 with a smooth exterior that is comfortable upon contact with the user's skin.

The skins 72 and 74 have little or no affect on the reversible extensible character of the film 64. That is, the films 72 and 74 may simply fail or permanently distort upon elongation of the film 64 with little or no user perceptible difference in the stress and strain properties.

Referring to FIG. 1, the diaper 10 includes leg cuffs 76 secured to the longitudinal edges 22 and 24 of the diaper. The leg cuffs 76 may be formed of the same film 64 as the waist band 62. The leg cuffs 76 are disposed between the top sheet 28 and back sheet 30 of the diaper. The top and back sheets 28 and 30 are gathered or pleated in a known manner to allow for the elastic extension and contraction of the longitudinal edges of the diaper in the leg cuff region.

For convenience of illustration, the tabs 32, waist bands 62 and leg cuffs 76 are included in the diaper 10. Of course, any one or combination of these features may be used in a diaper in accordance with the invention.

A modified tab in accordance with the invention is shown in FIG. 5. For convenience, modified elements are identified with the same reference numeral with the addition of a prime designation.

Referring to FIG. 5, a two piece tab or fastener assembly 32' includes a modified release tape 42' that is mounted onto the inside surface 14 of the diaper 10. The fastening tape 36 is identical to that described above, but it is mounted directly to the outside surface 16 of the diaper 10. The outboard end of the release tape 42' extends onto the inside face 40 of the tape 36, and the adhesive layers 54' and 48' may be joined to improve the Y-bond strength. As in the first embodiment, the tape 36 includes a plurality of elastic lanes 60 that are fixed as part of the factory joint.

Referring to FIG. 6, a diaper 10' in accordance with another embodiment of the present invention is shown. For convenience, corresponding elements are identified with the same reference numeral as in the first embodiment with the addition of a prime designation.

The diaper 10' includes a stretchable ear or wing 80 mounted adjacent the longitudinal edge 24' of the diaper end 18'. The wing 80 is secured to the longitudinal edge 24' of the diaper in any convenient manner, for example, sonic welding or adhesives. A similar wing (not shown) is mounted adjacent to longitudinal edge 22'. The stretchable wing arrangement provides waist tension and an elastic waist band is generally not necessary.

The diaper 10' includes a mechanical fastener arrangement comprising a hook tab 82 and a landing zone loop tab 84. Of course, any of the known mechanical fastener elements may be used to provide the fastener arrangement. As indicated above, the first embodiment may have a similar mechanical fastener instead of the illustrated adhesive fastener.

Referring to FIG. 7, the hook tab 82 includes an inelastic substrate 86 having hook members 88 projecting therefrom for engagement with the loop tab 84. The hook tab substrate 86 is secured to the wing 80 by an adhesive layer 90 or in another suitable manner.

The wing 80 is formed of a film 92 having alternate inelastic portions 94 and elastic portions 96. The film 92 includes a skin 98 extending along only one surface. The skin 98 may be formed of the same polymer forming the inelastic portions 94.

Figure 8:
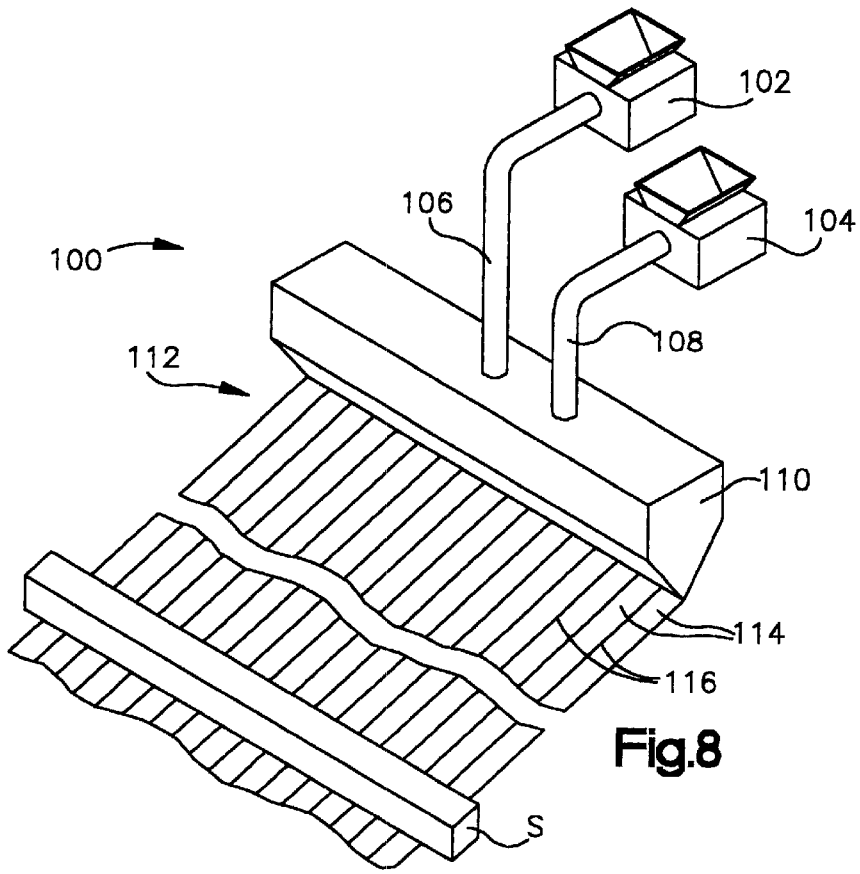
FIG. 8 is a schematic perspective view showing a coextrusion apparatus including a coextrusion die for making a flexible roll of film material in accordance with the invention.

Referring to FIG. 8, a coextrusion apparatus 100 which may be used to make the films 56, 64 and 92 in accordance with the invention is shown. This apparatus is described in greater detail in U.S. Pat. No. 4,435,141, the teachings of the patent being incorporated by reference.

Suitable polymer charges for forming inelastic and elastic films or lanes are respectively supplied to melt screw extruders 102 and 104. The polymer charges are melted in the extruders 102 and 104, and the molten polymers are forced at a predetermined pressure and temperature through lines 106 and 108 to a coextrusion die 110.

The polymer charges are heated to temperatures that sufficiently reduce the polymer viscosity to allow transportation and extrusion. The extrusion temperatures do not exceed that which would result in thermal degradation of the polymers.

A confluence of the molten polymers is extruded as a multilayer and multi-component film 112. The film 112 may be contacted with a casting roll (not shown) for initial cooling and further processed in a conventional manner. Although it is not part of the extrusion process, the film 112 may be pattern coated with adhesive in a known manner at adhesive coating station "S". For example, adhesive layers 48 and 50 may be applied at spaced locations along the width of the film 112.

Figure 9:
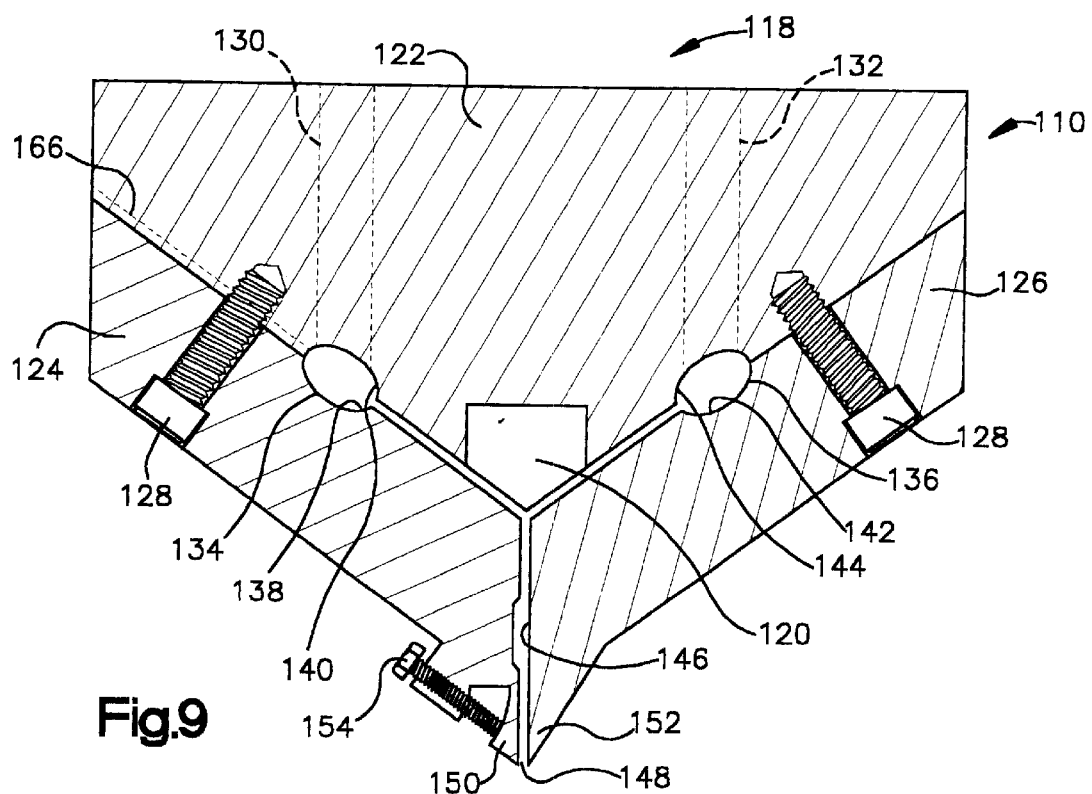
FIG. 9 is a cross-sectional view on an enlarged scale of the coextrusion die shown in FIG. 8.

Referring to FIG. 9, a cross-sectional view of the coextrusion die 110 is shown. The coextrusion die 110 includes an elongate body member 118 and a similarly elongate die bar 120. The die 110 may itself comprise a body block 122 and two opposing body sections 124 and 126. The opposing body sections 124 and 126 may be held to the body block 122 by a plurality of bolts 128.

The body block 122 may be formed with first and second conduits 130 and 132 (shown in dotted outline) for respectively conducting a molten thermoplastic polymer feed to a manifold 134 and a molten thermoplastic elastomer feed to a manifold 136.

The body section 124 is formed with a manifold surface 138 for cooperating with a surface 140 of the body block 122 to form a first manifold for longitudinally distributing the thermoplastic polymer feed. In a similar manner, body section 126 is formed with a manifold surface 142 that cooperates with another manifold surface 144 of the body block 122 to form a second manifold for longitudinally distributing the thermoplastic elastomer.

The body sections 124 and 126 cooperate to define a passage 146 for conducting the confluence of the polymers to an elongate die opening 148. The die opening 148 is defined by the adjacent lip portions 150 and 152 provided by the opposed body portions 124 and 126. The size of the die opening 148 may be adjusted by operation of screw 154.

Figure 10:
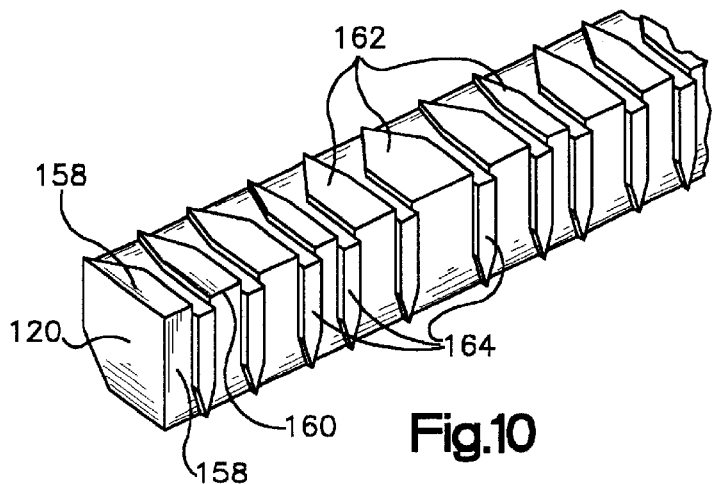
FIG. 10 is a perspective view of a die bar from the coextrusion die of FIG. 9.

Referring to FIG. 10, the die bar 120 includes intersecting die bar faces 156 and 158. The faces 156 and 158 intersect at a common notched edge 160. Projections 162 and 164 are formed in each of the faces 156 and 158. The projections 162 and 164 split the flow of polymer charge from associated manifolds 134 and 136 into separate streams which are interspersed adjacent to the edge 160 to form the coextruded film 112 with alternate lanes or stripes of the polymers. The projections 162 and 164 may be sized and spaced along the surfaces 156 and 158 to provide desired patterns and lane widths.

The film may be provided with a continuous skin on one or both surfaces thereof by means of inserting a shim between the body block 122 and one or both of the body sections 124 and 126. A shim 166 is shown in dotted outline disposed between the body block 122 and the body section 124. The shim 166 causes a thermoplastic skin to be formed on one surface of the film 112. The skin thickness may be varied by use of shims of suitable thicknesses.

Figure 11:
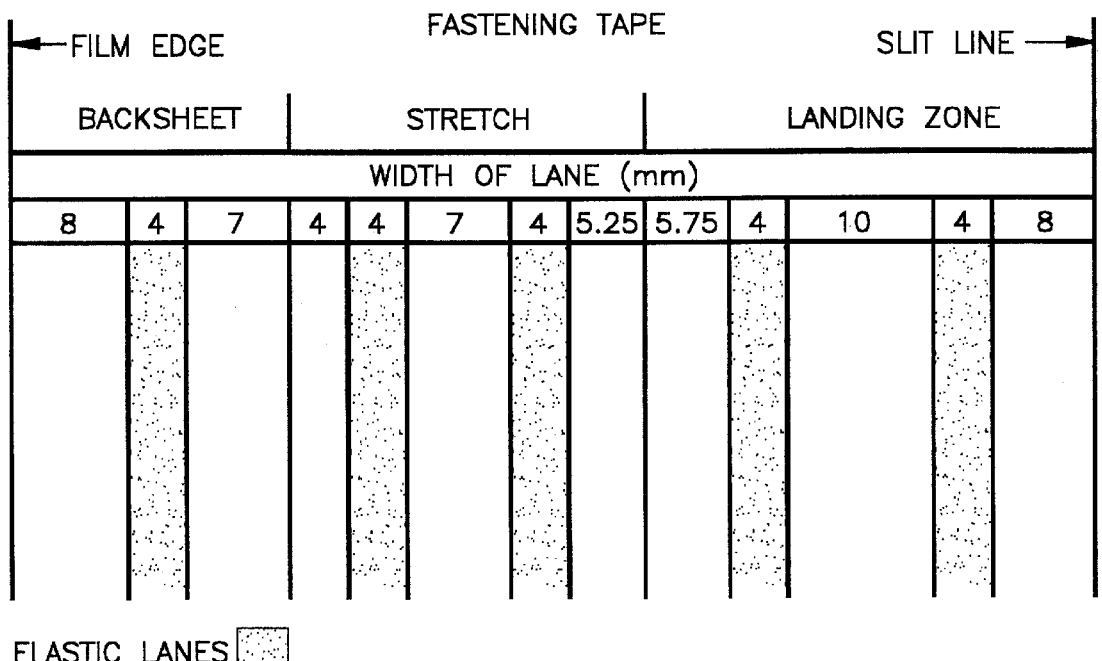
FIG. 11 is a graphic representation of the lane widths of a coextruded film material in accordance with the invention.

Referring to FIG. 11, a graphic representation of a repeating array of lane widths for roll stock of film material, such as film 112, is shown. The illustrated lane widths are selected for use in the manufacture of diaper tapes, such as the fastening tape 36 of the tab 32.

In this example, the fastening tape 36 has a total length of 75 mm extending in the cross direction of the roll stock. The intended diaper attachment locations or allocated cross direction extents in accordance with the functions of the various portions of the fastening tape in a diaper application are indicated in FIG. 11.

Accordingly, a first terminal segment or factory joint portion of the diaper tape to be secured to the diaper back sheet 30 (directly or via a release tape) includes two inelastic lanes and a center elastic lane. This back sheet portion of the fastening tape will be coated with a suitable adhesive, e.g. adhesive 48 at station S in FIG. 8, for permanent attachment to the diaper 10.

The central stretch segment or portion of the fastening tape includes a central inelastic lane disposed between two elastic lanes. An inelastic lane is provided at each of the extremities of the stretch portion. The two elastic lanes provide substantially all of the tape elasticity or stretch in the diaper application. Of course, other combinations of lanes and lane types may be used.

The second terminal segment or landing zone portion of the tape contains an array of elastic and inelastic lanes similar to that used in the stretch portion. The landing zone portion of the tape is slightly larger than the stretch portion, and it is intended to be positioned on the landing zone of the diaper for engagement therewith. Accordingly, the second terminal segment or landing zone portion of the tape may be coated with a suitable adhesive, e.g. adhesive layer 50 at station S in FIG. 8, or provided with a mechanical fastener for diaper closure.

The film edge of the roll stock material is shown at the left in FIG. 11, and the slit line is shown at the right. It should be appreciated that the fastening tape array shown in FIG. 11 may be repeated many times across the full width of the film material of the roll stock. For example, the array will be repeated 20 times for 1500 mm wide roll stock material.

The following films were prepared using a coextrusion apparatus as described above and alternating inelastic and elastic lanes as shown in FIG. 11. The thermoplastic elastomers used to make the elastic lanes are identified in Table 1 together with the end blocking resin, if added. The inelastic lanes were formed of PROFAX 8523, a high impact polypropylene supplied by Montell USA. The polymers were charged to the coextrusion apparatus and the films were coextruded at various thicknesses. The roll stock material had a width of about 20 inches or 508 mm, and in many cases acceptable roll conformation was obtained in these cases. (At 60 inches or 1500 mm roll width, similar or better results are obtained.) However, preferred results were obtained with the tetrablock elastomers having an end block reinforcing resin. Diaper tabs were cut in the cross direction from the films to prepare examples 1–27.

TABLE 1

| Example No. | Rubber Polymer | Endblocking Resin | RATIO |
|---|---|---|---|
| 1 | GRP 6906[1] | — | — |
| 2 | GRP 6906 | CUMAR LX 509[2] | 96/4 |
| 3 | GRP 6906 | CUMAR LX 509 | 92/8 |
| 4 | GRP 6906 | CUMAR LX 509 | 88/12 |
| 5 | G1730[3] | — | — |
| 6 | G1730 | BHPP 820[4] | 97/3 |
| 7 | G1730 | CUMAR LX 509 | 96/4 |
| 8 | G1730 | CUMAR LX 509 | 92/8 |
| 9 | G1730 | CUMAR LX 509 | 88/12 |
| 10 | G1730 | CUMAR LX 509 | 75/25 |
| 11 | G1730 | PPE[5] | 97/3 |
| 12 | G1730 | PPE | 97/3 |
| 13 | G1730 | EXXACT 4033[6] | 80/20 |
| 14 | GRP 6906 | EXXACT 3128[7] | 80/20 |
| 15 | SEPTON 2043[8] | — | — |
| 16 | SEPTON 2043 | CUMAR LX 509 | 92/8 |
| 17 | SEPTON 2043 | CUMAR LX 509 | 82/16 |
| 18 | SEPTON 2063[9] | — | — |
| 19 | GRP 6906 | — | — |
| 20 | G1730 | CUMAR LX 509 | 80/20 |
| 21 | G6906 | CUMAR LX 509 | 90/10 |
| 22 | G1730 | CUMAR LX 509 | 80/20 |
| 23 | G6906 | — | — |
| 24 | G6906 | — | — |
| 25 | G1730 | — | — |
| 26 | G6906 | CUMAR LX 509 | 90/10 |
| 27 | G1652[10] | EPR[11] | 95/5 |

[1]GRP 6906 is a styrene/ethylene-propylene/styrene triblock polymer sold by Shell Chemical Company.
[2]CUMAR LX 509 is a coumarone-indene resin used as an end block reinforcing resin herein, sold by Neville Chemical Company.
[3]G1730 is a SEPSEP styrene/ethylene-propylene/styrene/ethylene-propylene tetra block copolymer sold by Shell Chemical Company.
[4]BHPP 820 is a polyphenyl ether resin having a molecular weight of 36,000 used as an end block reinforcing resin herein, sold by General Electric Company.
[5]PPE is a polyphenyl ether resin having a molecular weight of 4,000 used as an end block reinforcing resin herein.
[6]EXXACT 4033 is a metallocene plastomer comprising a high density rubbery polyolefin used herein as an end block reinforcing resin, sold by Exxon.
[7]EXXACT 3128 is a metallocene plastomer comprising a low density rubbery polyolefin that blends with the rubber, sold by Exxon.
[8]SEPTON 2043 is a SEPS styrene/ethylene-propylene/stryrene triblock polmer, sold by Kuraray Chemical of Japan.
[9]SEPTON 2063 is a SEPS styrene/ethylene-propylene/stryrene triblock polmer, sold by Kuraray Chemical of Japan.
[10]G1652 is a SEBS styrene/ethylene-butylene/styrene triblock copolymer sold by Shell Chemical Company.
[11]EPR is an ethylene-propylene copolymer rubber having a grade designation EPM 306, that blends with the rubber, sold by Bayer.

The calipers and widths of the diaper tabs of examples 1–27 were measured and the results are reported in Table 2 below. The end block reinforcing agents enabled thicknesses ranging from 3 to 8.5 mils as measured in the elastic or rubber portions of the films.

The shear strengths of the diaper tabs of examples 1–27 were measured in a lengthwise direction at 100° F. using a 500 gram static shear load. The area of the elastic or rubber portions of each tab between the test jaw and the applied static load was measured. The static load was allowed to hang until the tab failed. Three samples were tested in each case, and the average times to failure are reported in minutes. The elastic area was substantially identical for each of the three samples of each example, and a single rubber area is reported.

In order to relate the failure time to the elastic or rubber portion of the film, the ratio of (1) the average minutes to failure to (2) the elastic or rubber cross-sectional area is reported as a normalized shear value.

TABLE 2

| Example No. | Caliper (mils) | Elastomer Width (inches) | Elastomer Cross-Sectional Area (mils$^2$/1 in. tab) | Shear (Minutes) | Shear (normalized to unit cross-sectional area) |
|---|---|---|---|---|---|
| 1 | 4.8 | 1/2 | 2400 | 290 | 0.1207 |
| 2 | 4.4 | 5/8 | 2750 | 442 | 0.1608 |
| 3 | 4 | 3/8 | 1500 | 1224 | 0.8160 |
| 4 | 4.4 | 3/8 | 1650 | 2718 | 1.6473 |
| 5 | 4.6 | 1/4 | 1150 | 208 | 0.1806 |
| 6 | 4 | 7/32 | 876 | 89 | 0.1020 |
| 7 | 4.5 | 6/32 | 846 | 719 | 0.8495 |
| 8 | 4.3 | 7/32 | 942 | 780 | 0.8277 |
| 9 | 4.3 | 10/32 | 1344 | 4175 | 3.1064 |
| 10 | 4.8 | 7/32 | 1051 | 4175 | 3.9724 |
| 11 | 7 | 11/32 | 2406 | 1563 | 0.6496 |
| 12 | 3 | 10/32 | 936 | 177 | 0.1891 |
| 13 | 3.5 | 7/32 | 766 | 70 | 0.0914 |
| 14 | 5.2 | 11/32 | 1789 | 5429 | 3.0345 |
| 15 | 3.6 | 11/32 | 1238 | 70 | 0.0565 |
| 16 | 6.3 | 5/32 | 983 | 1295 | 1.3174 |
| 17 | 8.5 | 4/32 | 1062 | 5487 | 5.1667 |
| 18 | 6.4 | 4/32 | 800 | 97 | 0.1208 |
| 19 | 4 | 11/32 | 1376 | 417 | 0.3031 |
| 20 | 3.2 | 15/32 | 1500 | 354 | 0.2358 |
| 21 | 4 | 11/32 | 1376 | 153 | 0.1114 |
| 22 | 3 | 15/32 | 1407 | 305 | 0.2165 |
| 23 | 6 | 4/32 | 750 | 681 | 0.9076 |
| 24 | 5.6 | 9/32 | 1574 | 408 | 0.2594 |
| 25 | 3.8 | 10/32 | 1186 | 107 | 0.0905 |
| 26 | 8.3 | 7/32 | 1818 | 2718 | 1.4950 |
| 27 | 8 | 9/32 | 2248 | 1 | 0.0006 |

The mode of shear failure of the examples is related to the relative strength of the joint. The tetrablock elastomers typically result in failure occurring within the rubber as opposed to at the joint. On the other hand, the triblock elastomers also tend to fail in the rubber, but there are limited occurrences of joint failure. It should be appreciated that the inelastic or polyolefin may be combined or modified to increase its compatibility with the rubber or elastomers as by incorporation of similar hydrocarbon components, e.g. ethylene-propylene.

A most important factor in the improvements in joint strength is the type of elastic polymer or rubber used. For example, SI, SIS, SB, SBS, SEB, SEBS, SEP and SEPS thermoplastic elastomers were tested in combination with a polyolefin. (The foregoing letter notations are used in a conventional manner to identify polymer blocks with S being styrene, I being isoprene, B being butylene, EB being ethylene-butylene and EP being ethylene-propylene.) The following resulted:

SI(S) rubbers have poor joint strength and degrade in a short time at typical polyolefin extrusion temperatures;

SB(S) rubbers exhibit better joint strengths than SI(S), but not as good as SEPSEP;

SB(S) rubbers have the highly undesirable property of cross linking on exposure to polyolefin extrusion temperatures; and SEB(S) rubbers have good stability at polyolefin extrusion temperatures and joint strengths better than SI(S), but not as good as SEPSEP.

Only when the thermoplastic elastomer contained SEPSEP tetrablock elastomer was it observed that superior joint strength and uniform, as well as low calipers, were achieved. These improvements over triblock are believed to be related to several factors. Firstly, the tetrablock polymer has a lower viscosity than a triblock of similar molecular weight, and the tetrablock polymer softens and breaks-up at a lower temperature than triblock polymer. This results in an elastomer with better melt extrusion properties. Secondly, one end of the fourth (D) block, the "tail" of the polymer, is not tied to an immobile styrene endblock and it therefore has greater molecular mobility than a midblock (B) which is tied at both ends to a styrene block. This greater mobility allows the tail to more freely associate with molecules such as the EPR impact modifier in a polypropylene resin and ultimately leads to a more intimate bond between the elastomer lane and thermoplastic lane than is possible with the triblock-based elastomer.

Herein, a tetrablock polymer with ethylene-propylene rubber segments is favored. For example, KRATON G1730 is a SEPSEP block polymer containing about 19 to 21 percent styrene by weight, the styrene blocks having a molecular weight of about 12,000. The styrene blocks give the rubber its thermoplastic character and strength. The styrene blocks are connected by the ethylene-propylene blocks. The ethylene-propylene block is believed to impart rubbery characteristics to the polyolefin and/or inhibit crystallization. The ethylene-propylene block is also believed to inhibit fracture propagation and improve flex characteristics. The terminal ethylene-propylene block provides a tail-like extension beyond the adjacent styrene.

It is observed that there is no distinct boundary between the polyolefin and SEPSEP elastomer when the joint is stretched in a transverse direction. The polyolefin and the elastomer appear to blend together at the joint, and this is believed to be due to the similarity in structure of the polyolefin and the ethylene propylene tail of the tetrablock which in turn is believed to give the good joint strength.

The joint strength is sufficiently good that a typical tensile test shows elongation of the polypropylene before the joint separates. Also, in such a tensile test, the polypropylene begins to neck down in thickness immediately adjacent to the joint prior to failure. (The elastomer is still at its extruded thickness.) The joint may not be stronger than the polypropylene in bulk or on average, but it appears to be stronger than the polypropylene in the neck down thickness portion. In typical tensile tests pulling a one inch wide tab at 20 inches per minute, the polypropylene breaks before the joint. The joint exceeds the strength of the polypropylene since the polypropylene yields without joint failure.

The boundary between the polyolefin and elastomer lanes is not planar, but rather, it typically has an oval cross-sectional shape as indicated in FIG. 4. The elastomer may have any elongated or flattened oval shape cross-section. Specific cross-sectional shapes depend upon the selection of rubber and polyolefin.

The improvements in high temperature shear strength are believed to be associated with the interaction of the end block reinforcing agent and the end block of the rubber. When end block reinforcing agents are mixed with SIS, SB or SEP rubbers they associate with the end block, enlarge it and help to give it cohesive strength. The end block of styrene in a rubber block polymer may have a molecular weight of from 10,000 to 20,000. Addition of an end block reinforcing agent may change the total mass of that styrene block to 40,000.

The end block reinforcing agent may also improve the crystalline character of the styrene end block of the rubber and thereby raise its melting temperature. Of course, other additives having a relatively higher melting temperature than the end block increase the average melting temperature through physical mixture and average molecular weight increases.

The relative amount of the reinforcing end block agent affects the relative calipers of the polyolefin and elastomer. More particularly, a relatively higher molecular weight styrene block causes increased die swell during extrusion and an increased final film gauge in the elastomer or rubber area. For example, a test of the polymers in the U.S. Pat. No. 4,787,897, supra, without reinforcing resins resulted in a large amount of die swell. This is believed to be due to be large styrene blocks in the triblock polymers used in the '897 patent. Large styrene blocks swell and make it extremely difficult to extrude a flat film. Consequently, the films had large bulges where the rubber lanes are located.

The tetrablock polymers have smaller end blocks, and when coextruded by itself, it comes out about half as thick as the polypropylene. Upon addition of a small amount of reinforcing resin to improve the elevated temperature shear, it was found to be just about the amount needed to cause rubber to extrude at the same caliber as the polypropylene. ENDEX-160, a polycyclic arene reinforcing agent sold by Hercules having a softening point of 160° C., can be used at levels of 5 to 25 percent by weight. At 14% resin and 86% rubber, the elastomer is thicker than polyolefin, but at 8% resin and 92% rubber, the elastomer is thinner than polyolefin. Accordingly, somewhere in the middle of that range there is an optimum.

The optimum for shear strength is actually a little higher than 14 percent, and it does not coincide with the optimum uniform caliper. However, somewhere in the window, sufficient shear strength is achieved for diaper tape applications. Similarly, optimum formulations for other applications may be determined quickly with routine trial and error sampling techniques.

Another advantage of the KRATON G1730 tetrablock rubber is that at or about the amount that gives uniform extrusion properties as between polyolefin and rubber as well as good elevated temperature shear, the resulting elasticity or stress/strain character is substantially equal to that desired in a diaper tab. A preferred diaper tab elasticity is 3.5 lbs. force for a 1" wide tab at 100% elongation.

Using coextrusion apparatus as shown in FIGS. 7–9 to make a polypropylene and SEPSEP roll of film stock material having a 1500 mm or 60 inch width, the film thickness was measured at each elastic lane across the film width. The skin was continuous and varied in thickness from about 7 microns to about 25 microns. The thin skin is believed to be due in part to the compatibility between the rubber and the polyolefin, with the skin tending to diffuse into the rubber. The skin provides only the slightest deviation in stress/strain testing.

In the foregoing film, the thicknesses of the rubber lanes varied from about 180 microns to about 250 microns across the film width. The alternate lanes of polypropylene were of thicknesses similar to those of the rubber lanes. Relatively thin films, e.g. 3 mils or less, are possible with the use of the tetrablock polymers and end block reinforcing agents in accordance with the invention. In comparison, the teachings of U.S. Pat. No. 4,787,897, supra, did not enable production of films less than about 8 to 12 mils in thickness.

The invention is not restricted to the slavish imitation of each and every detail set forth above. Obviously, devices may be provided which change, eliminate, or add certain specific details without departing from the invention.

What is claimed:

1. A method of making a reversibly extensible fastening tape substrate comprising providing first and second charges of film-forming polymer, said first charge comprising a thermoplastic elastomer and said second charge comprising a thermoplastic polymer, said thermoplastic elastomer comprising a block polymer of molecules having rubbery segments and non-rubbery segments, said block polymer including terminal end segments formed of said rubbery segments, coextruding said charges of polymer to form a roll stock material with alternate discrete elastic lanes formed of said thermoplastic elastomer and inelastic lanes formed of said thermoplastic polymer, said roll stock material having a machine direction and a cross direction with said lanes extending in said machine direction, forming said tape substrate from said roll stock material so that said tape substrate has a length extending in the cross direction of said roll stock material and a width extending in the machine direction of said roll stock, said tape including terminal end portions connected by a central portion located along said length of said tape, sizing said tape substrate and said lanes so that said tape substrate has at least two spaced elastic lanes extending across the width of said tape substrate within said central portion which distribute shear loads applied to said tape substrate and inhibit propagation of tearing failures.

2. The method of claim 1, wherein said fastening tape includes terminal end portions connected by a central portion located along said length of said fastening tape, said terminal portions being adapted to secure said tape to a surface, and at least a third elastic lane extends across at least one of said terminal portions.

3. The method of claim 2, wherein said elastic lane has a width of from about 1/16 to about 1.0 inch and said inelastic lane has a width in the range of from about 1/16 to 2.0 inches.

4. The method of claim 3, wherein said thermoplastic elastomer is a tetrablock polymer of ABAD structure wherein A is a vinyl aromatic hydrocarbon polymer block, and B and D are conjugated diene polymer blocks.

5. The method of claim 4, wherein said thermoplastic elastomer is a tetrablock polymer of ABAD structure wherein A is selected from the group consisting of styrene and alkyl substituted styrene, and B and D, which may be the same or different, are selected from the group consisting of hydrogenated butadiene polymer block and hydrogenated isoprene polymer block.

6. The method of claim 5, wherein an aromatic end block reinforcing resin is added to said charge of thermoplastic elastomer to increase the elevated temperature shear strength of said thermoplastic elastomer.

7. The method of claim 1, wherein said step of coextruding said charges further includes coextruding at least one skin layer of said thermoplastic polymer.

8. A method of making a reversibly extensible stretchable film comprising providing first and second charges of film-forming polymer, said first charge comprising a tetrablock thermoplastic elastomer and said second charge comprising a thermoplastic polymer, said tetrablock thermoplastic elastomer includes rubbery segments and non-rubbery segments, and said tetrablock thermoplastic elastomer has a terminal end formed of said rubbery segments, coextruding said charges of polymer to form a roll construction film material with alternate discrete elastic lanes formed of said tetrablock thermoplastic elastomer and inelastic lanes formed of said thermoplastic polymer, forming said stretchable film from said construction film so that said stretchable film has a length and a width respectively extending in the cross direction and the machine direction of said construction film.

9. The method of claim 8, wherein said rubbery segment includes ethylene-propylene.

10. The method of claim 9, wherein said non-rubbery segment is selected from the group consisting of substituted and unsubstituted vinyl arenes.

11. The method of claim 8, wherein said tetrablock thermoplastic elastomer has an ABAD structure wherein A selected from the group consisting of styrene and alkyl substituted styrene, and B and D, which may be the same or different, comprise conjugated dienes.

12. The method of claim 8, wherein said tetrablock thermoplastic elastomer has an ABAD structure wherein A is selected from the group consisting of styrene and alkyl substituted styrene, and B and D, which may be the same or different, are selected from the group consisting of hydrogenated butadiene polymer block, hydrogenated ethylene-propylene and hydrogenated isoprene polymer block.

13. The method of claim 8, wherein said tetrablock thermoplastic elastomer is SEPSEP tetrablock polymer.

14. The method of claim 8, wherein an aromatic end block reinforcing resin is added to said thermoplastic elastomer in an amount equal to from about 8 percent to about 14 percent based on the total weight of said resin and polymer.

15. The method of claim 8, wherein an aromatic end block reinforcing resin is added to said thermoplastic elastomer in an amount sufficient to increase the elevated temperature shear strength and to cause said elastic and inelastic lanes to be of substantially equal thickness.

16. The method of claim 15, wherein said end block reinforcing resin is selected from the group consisting of polyphenylene oxides and polycyclic arenes.

17. The method of claim 8, wherein said stretchable film also includes at least one skin layer of said thermoplastic polymer that substantially covers said elastic lanes.

18. The method of claim 8, wherein said step of coextruding said charges further includes coextruding at least one skin layer of said thermoplastic polymer.

19. A method of making film roll stock to be cut to form stretchable films including a stretch zone connected to a non-stretch zone comprising the steps of first and second charges of film-forming polymer, said first charge comprising a thermoplastic elastomer and said second charge comprising a thermoplastic polymer, said thermoplastic elastomer comprising a block polymer of molecules having rubbery segments and non-rubbery segments, said block polymer including terminal end segments formed of said rubbery segments, coextruding said charges of film-forming polymer to form said film roll stock with elastic lanes formed of said thermoplastic elastomer and inelastic lanes formed of said thermoplastic, said lanes being integrally joined and extending in said machine direction, forming said stretchable film with its length and width extending respectively in the cross direction and the machine direction of said film roll stock, and sizing said stretchable film and said lanes so that said stretchable film has at least one elastic lane extending across the width of said stretchable film within said non-stretch zone to increase the uniformity of the distribution of elastic and inelastic lanes in the cross direction of said film roll stock and to thereby improve roll conformation of said film roll stock.

20. The method of claim 19, wherein said thermoplastic elastomer has a tetrablock ABAD structure wherein A selected from the group consisting of styrene and alkyl substituted styrene, and B and D, which may be the same or different, comprise conjugated dienes.

21. The method of claim 20, wherein an aromatic end block reinforcing resin is added to said thermoplastic elastomer in an amount equal to from about 5 percent to about 25 percent based on the weight of said thermoplastic elastomer.

22. The method of claim 19, wherein said step of coextruding said charges further includes coextruding at least one skin layer of said thermoplastic polymer.

\* \* \* \* \*